US011096800B2

(12) United States Patent
Harper et al.

(10) Patent No.: US 11,096,800 B2
(45) Date of Patent: Aug. 24, 2021

(54) JOINT PROSTHESIS WITH REMOVAL DEVICE

(71) Applicant: MEDACTA INTERNATIONAL SA, Castel San Pietro (CH)

(72) Inventors: Wade Harper, Castel San Pietro (CH); Ralph Hertel, Castel San Pietro (CH); Volkmar Jansson, Castel San Pietro (CH); Bernhard Jost, Castel San Pietro (CH); Christophe Monnin, Castel San Pietro (CH); Peter Müller, Castel San Pietro (CH); Matthew D. Saltzman, Castel San Pietro (CH); Anup Shah, Castel San Pietro (CH); Matthias A. Zumstein, Castel San Pietro (CH); Francesco Siccardi, Castel San Pietro (CH); Massimiliano Bernardoni, Castel San Pietro (CH); Andrea Rosa, Castel San Pietro (CH)

(73) Assignee: MEDACTA INTERNATIONAL SA, Castel san Pietro (CH)

( * ) Notice: Subject to any disclaimer, the term of this patent is extended or adjusted under 35 U.S.C. 154(b) by 165 days.

(21) Appl. No.: 15/541,767

(22) PCT Filed: Dec. 10, 2015

(86) PCT No.: PCT/IB2015/059503
§ 371 (c)(1),
(2) Date: Jul. 6, 2017

(87) PCT Pub. No.: WO2016/110758
PCT Pub. Date: Jul. 14, 2016

(65) Prior Publication Data
US 2018/0021150 A1 Jan. 25, 2018

(30) Foreign Application Priority Data
Jan. 8, 2015 (IT) .......................... MI2015A000005

(51) Int. Cl.
*A61F 2/40* (2006.01)
*A61F 2/30* (2006.01)
*A61F 2/46* (2006.01)

(52) U.S. Cl.
CPC .............. *A61F 2/4637* (2013.01); *A61F 2/30* (2013.01); *A61F 2/4081* (2013.01);
(Continued)

(58) Field of Classification Search
CPC .... A61F 2/389; A61F 2/4609; A61F 2/30988; A61F 2/38; A61F 2002/30484;
(Continued)

(56) References Cited

U.S. PATENT DOCUMENTS 5,217,497 A * 6/1993 Mehdian ............ A61B 17/1671
606/268
6,022,357 A 2/2000 Reu et al.
(Continued)

FOREIGN PATENT DOCUMENTS

EP 0951872 B1 2/2005
EP 2055273 A1 5/2009
(Continued)

OTHER PUBLICATIONS

International Search Report and Written Opinion dated Mar. 17, 2016 from International Application No. PCT/IB2015/059503, 12 pages.
(Continued)

*Primary Examiner* — Ann Schillinger
(74) *Attorney, Agent, or Firm* — Meunier Carlin & Curfman LLC (57) ABSTRACT

Joint prosthesis (100) with removal device comprising a first portion (10) suitable to be implanted in a bone structure and suitable to couple with a second portion (50), characterised in that said second portion (50) houses within it a removal
(Continued)

element (70) suitable to interact with at least one of said first and second portions (10, 50) and in that said removal element (70), is configured to be operated in translation with respect to the second portion (50), and to generate a detachment force such as to uncouple the first portion (10) from the second portion (50) of the joint prosthesis (100).

13 Claims, 10 Drawing Sheets

(52) U.S. Cl.
CPC .. *A61F 2/4612* (2013.01); *A61F 2002/30332* (2013.01); *A61F 2002/30878* (2013.01); *A61F 2002/4629* (2013.01); *A61F 2002/4638* (2013.01); *A61F 2002/4641* (2013.01)

(58) Field of Classification Search
CPC .. A61F 2002/30601; A61F 2002/30774; A61F 2002/30878; A61F 2002/4205; A61F 2/30942; A61F 2002/304; A61F 2002/3055; A61F 2002/30433; A61F 2002/30507; A61B 17/025; A61B 2017/564; A61B 17/0401; A61B 17/157; A61B 17/7032; A61B 2017/00477; A61B 2017/0256; A61B 2017/681; A61B 2017/8655
See application file for complete search history.

(56) References Cited

U.S. PATENT DOCUMENTS

| | | | |
|---|---|---|---|
| 6,063,123 | A | 5/2000 | Burrows et al. |
| 6,171,342 | B1 * | 1/2001 | O'Neil ................ A61F 2/38 |
| | | | 623/20.15 |
| 9,439,768 | B2 * | 9/2016 | Iannotti ................ A61F 2/4003 |
| 10,433,967 | B2 * | 10/2019 | Deransart ............ A61F 2/4014 |
| 2004/0064187 | A1 | 4/2004 | Ball et al. |
| 2008/0167722 | A1 * | 7/2008 | Metzger ................ A61F 2/385 |
| | | | 623/20.36 |
| 2016/0128841 | A1 * | 5/2016 | Dalla Pria ............ A61F 2/4059 |
| | | | 623/19.14 |

FOREIGN PATENT DOCUMENTS

| | | | | |
|---|---|---|---|---|
| EP | 2082705 | B1 | 4/2012 | |
| EP | 2777637 | A1 | 9/2014 | |
| FR | 2575383 | A1 | 7/1986 | |
| FR | 2807643 | A1 * | 10/2001 | ............ A61F 2/38 |
| GB | 1371335 | A | 10/1974 | |
| WO | 89/07917 | A1 | 9/1989 | |

OTHER PUBLICATIONS

Australian Examination Report dated Apr. 26, 2019, 5 pages.

* cited by examiner

JOINT PROSTHESIS WITH REMOVAL DEVICE

The present invention discloses a joint prosthesis with removal device. In the state of the art, there are known surgical prostheses adapted to be implanted in the body of a patient in order to replace the original joint, affected by particular pathologies and/or wear. Due to said pathologies or wear affecting the joints, the patient perceives pain during movement and the replacement of said joints makes it possible for him/her to return to a normal life, unburdened by pain during movements.

The surgical operation for the replacement of the natural joint with a new artificial joint involves specific intervention passages on the patient's bones in order to implant artificial bone coating surfaces and articulation elements between the two implanted artificial surfaces. Said artificial surfaces comprise essentially two parts: a first part, in contact with the patient's bone, and a second part, not in contact with the patient's bone but articulating with a joint element. The first part in contact with the bone is responsible for correctly securing the artificial surface to the patient's body and can present a portion thereof adapted to be inserted in a bone seat formed by the surgeon during implantation. Said artificial surface can also be fixed to the bone by means of various techniques; for example, it may be cemented or, alternatively, non-cemented.

The state of the art has a plurality of joint prostheses of this type for the main joints of the human body. For example, document U.S. Pat. No. 8,246,687 by Biomet Manufacturing Corporation can be mentioned about the shoulder joint; document WO2013074700 by Maxx Orthopedics Inc can be mentioned about knee joint; document US2014135939 by Wright Medical Tech Inc can be mentioned about ankle joint; and so on.

After replacing the natural joint as needed with a known prosthetic joint, the patient can resume his/her normal activities. Of course, it is possible that the normal activities of the patient can lead to wear of the joint prosthesis implanted or that, with time, said joint prosthesis requires operation of total or partial replacement. It will therefore be necessary to perform another surgery aimed at partial or total replacement of the previously implanted joint prosthesis.

As is clear, in this new surgery it will be necessary to disassemble the joint prosthesis from the patient's bone where it is implanted and replace it, possibly in part, with a new one. Depending on the methodology used for prosthesis implant, the removal operations of the same may be more or less invasive but, in any case, it will be necessary to act on the bone by means of appropriate instruments, such as, for example, burrs, saws or the like, in order to detach the joint replacement by said bone. It is clear to the skilled in the art that said replacement surgeries involve remarkable stresses transmitted to the bone, up to the removal of bone material in order to disassemble the prosthesis.

This type of procedure may be considered as a drawback to what known in the art. In fact, generally, the stresses imposed by the surgeon to detach the previously implanted prosthetic joint can damage the bone structure and cause issues to the patient.

Another drawback to what known in the prior art is the difficulty for the surgeon to uncouple the joint prosthesis from the patient's body. In fact, the surgeon has to operate in the presence of body fluids such as blood, and in confined spaces, due to the need to minimize the invasiveness of the surgery, circumstances that do not allow for optimal performance of the operations of detachment of the joint prosthesis from the bone.

A further drawback to what known in the prior art is the possibility that the surgeon exerts an excessive force during the operations of detachment of the prosthetic joint, therefore damaging the bone.

Another drawback to what known in the prior art is the need to employ a relatively long time to obtain an optimal detachment of the prosthetic joint, using different sterile surgical instruments with a consequent increase in costs for the structure and prolongation of the time required to complete the surgery.

Said drawbacks are common to all main joint prostheses i.e., for example, shoulder, elbow, wrist, knee, hip and ankle joint prostheses. In its general aspects, the present invention intends to solve the drawbacks of the known state of the art with reference to each type of joint prosthesis.

Thus, an object of the present invention is to provide a joint prosthesis removal device that can be uncoupled without damaging the patient's bone structure.

A further object of the present invention is to provide a joint prosthesis removal device which is easy to use for the surgeon, minimizing the invasiveness of the surgical operation.

A further object of the present invention is to provide a joint prosthesis removal device that is able to minimize the force imparted by the surgeon on the joint prosthesis to be removed.

A further object of the present invention is to provide a joint prosthesis removal device that is able to minimize the number of sterile surgical instruments which must be employed by the surgeon for decoupling the present invention from the patient's bone.

The final object of the present invention is to provide a joint prosthesis removal device that is able to reduce surgery costs and duration and is easy and cost-effective to use and implement.

In view of these objects, the present invention provides a joint prosthesis removal device, the essential feature of which constitutes the subject of claim 1.

Further advantageous features are listed in the dependent claims.

All claims are considered as described.

The present invention will be described in greater detail by way of example only with the aid of the accompanying drawings, in which.

In the drawing, 100 refers to a joint prosthesis with removal device according to the present invention. In the following description, explicit reference will be made to a glenoid joint prosthesis, as depicted in the accompanying drawing only by way of example, however not limiting the scope of the present invention only to this type of prosthesis.

Figure 1:
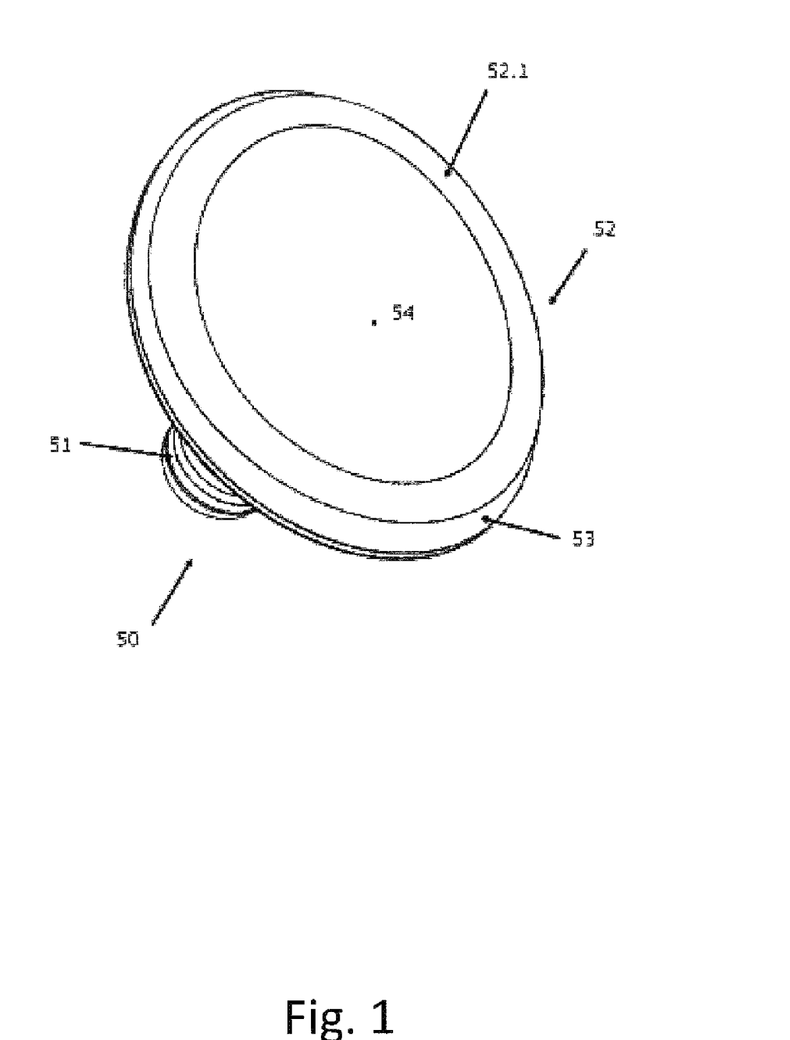
FIG. 1 is a ¾ front view of the upper portion of a joint prosthesis with removal device according to a preferred embodiment of the present invention.
Figure 2:
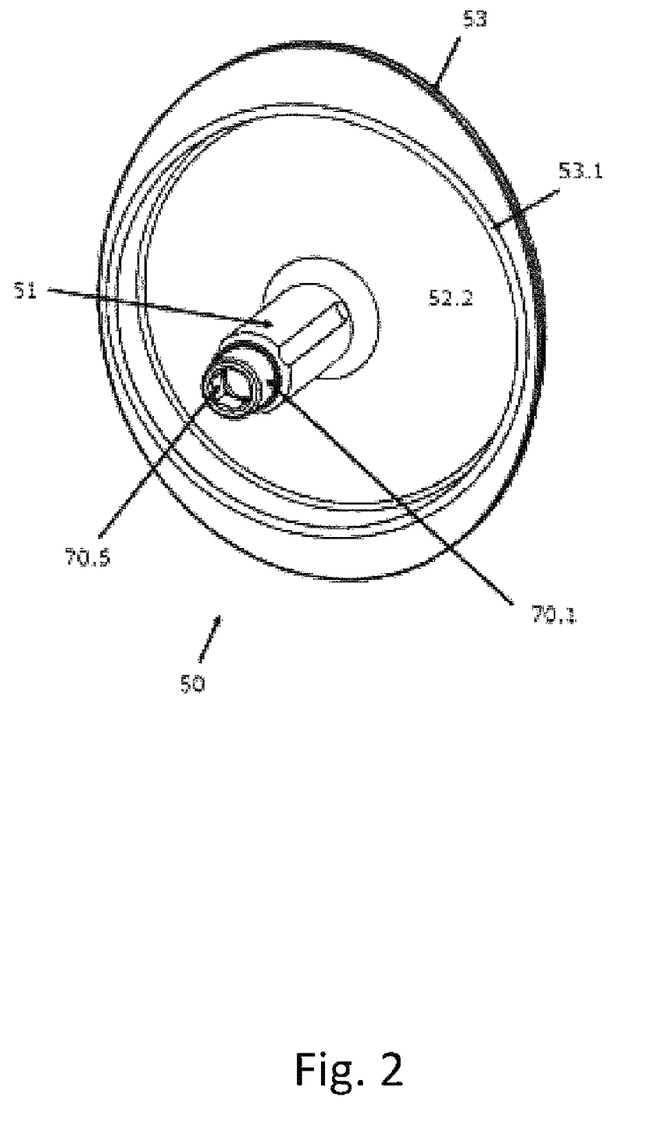
FIG. 2 is a ¾ backside view of the upper portion of a joint prosthesis with removal device according to a preferred embodiment of the present invention.
Figure 3:
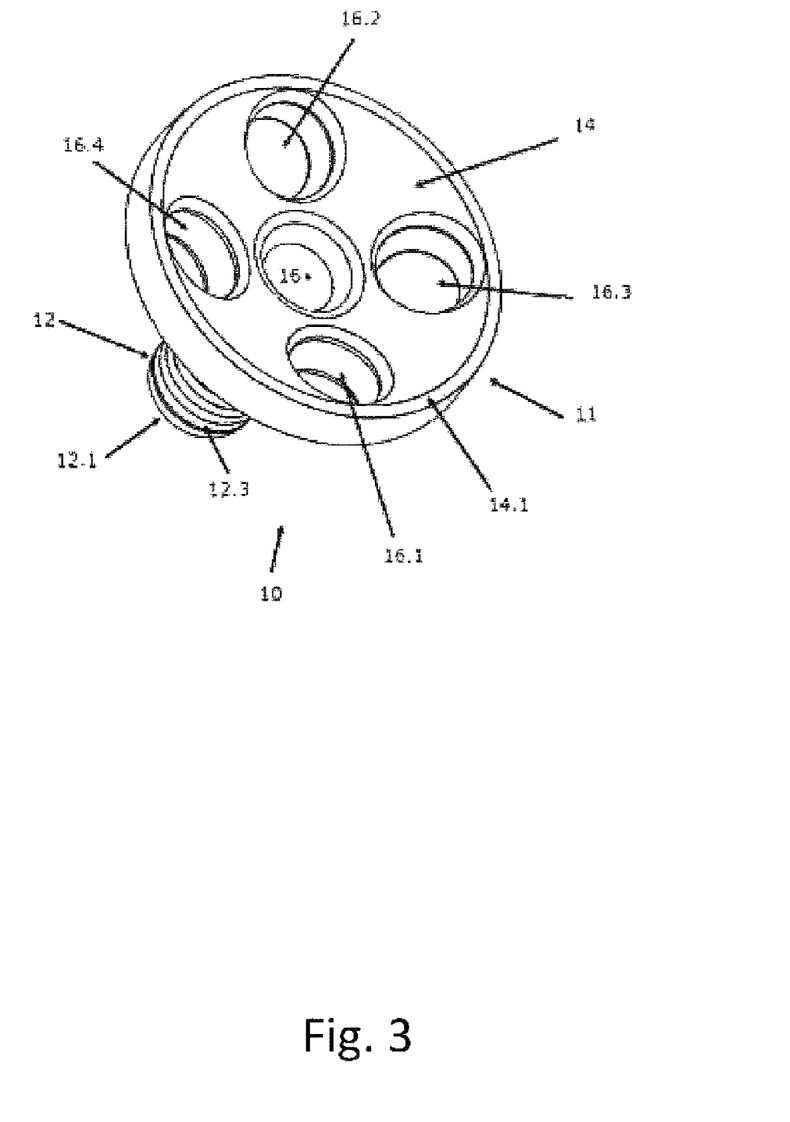
FIG. 3 is a ¾ front view of a lower portion of a joint prosthesis with removal device according to a preferred embodiment of the present invention.
Figure 4:
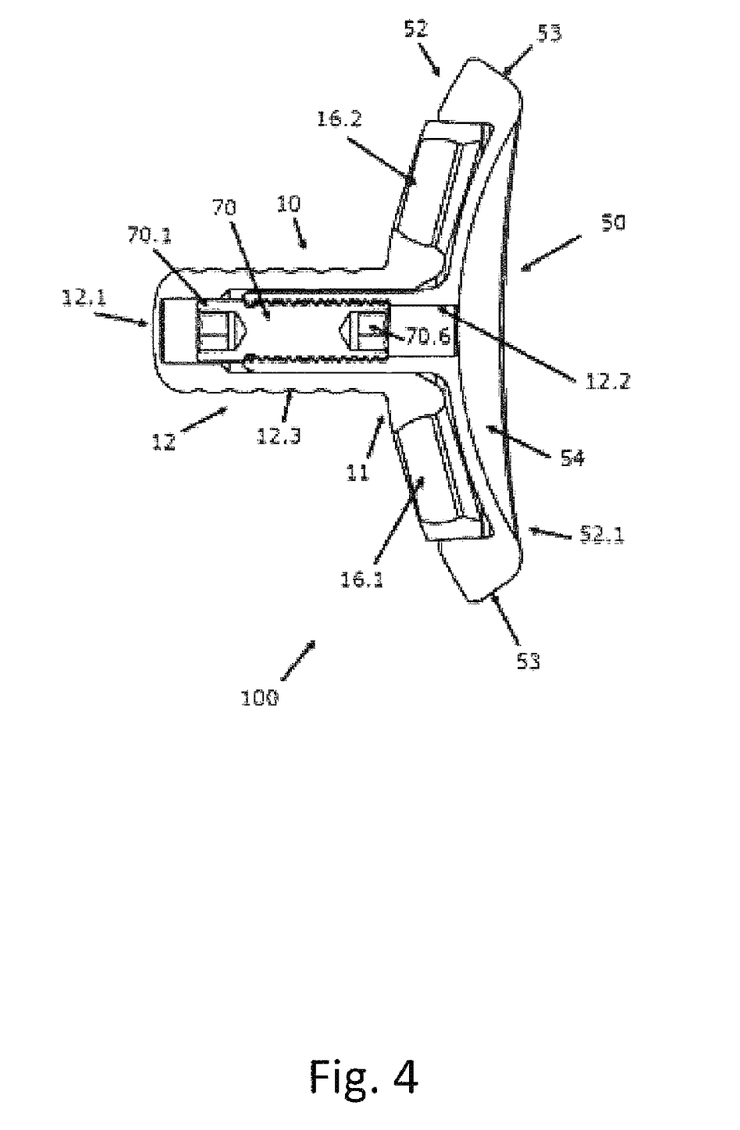
FIG. 4 is an axial sectional view of a joint prosthesis with removal device according to the preferred embodiment of the present invention.
Figure 5:
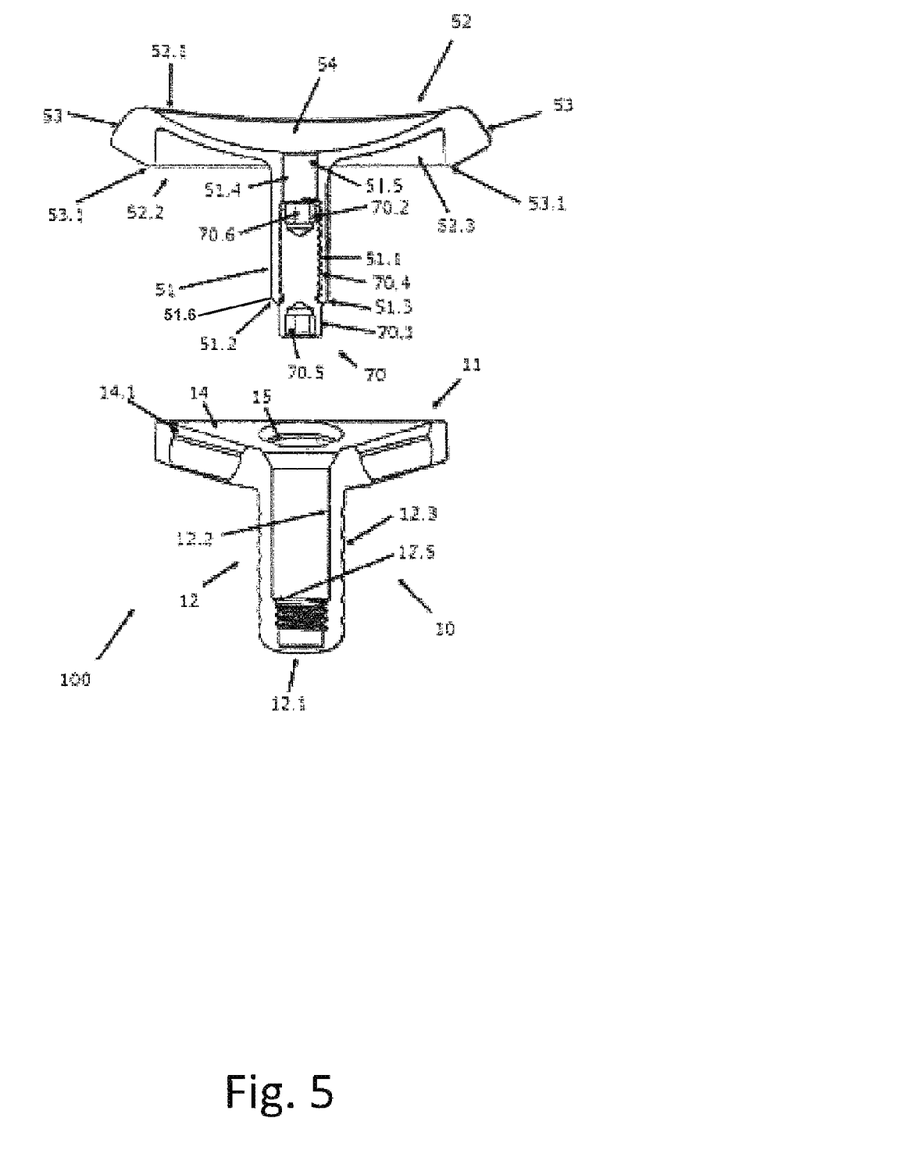
FIG. 5 is an axial, partially exploded sectional view of a joint prosthesis with removal device according to the preferred embodiment of the present invention.
Figure 6:
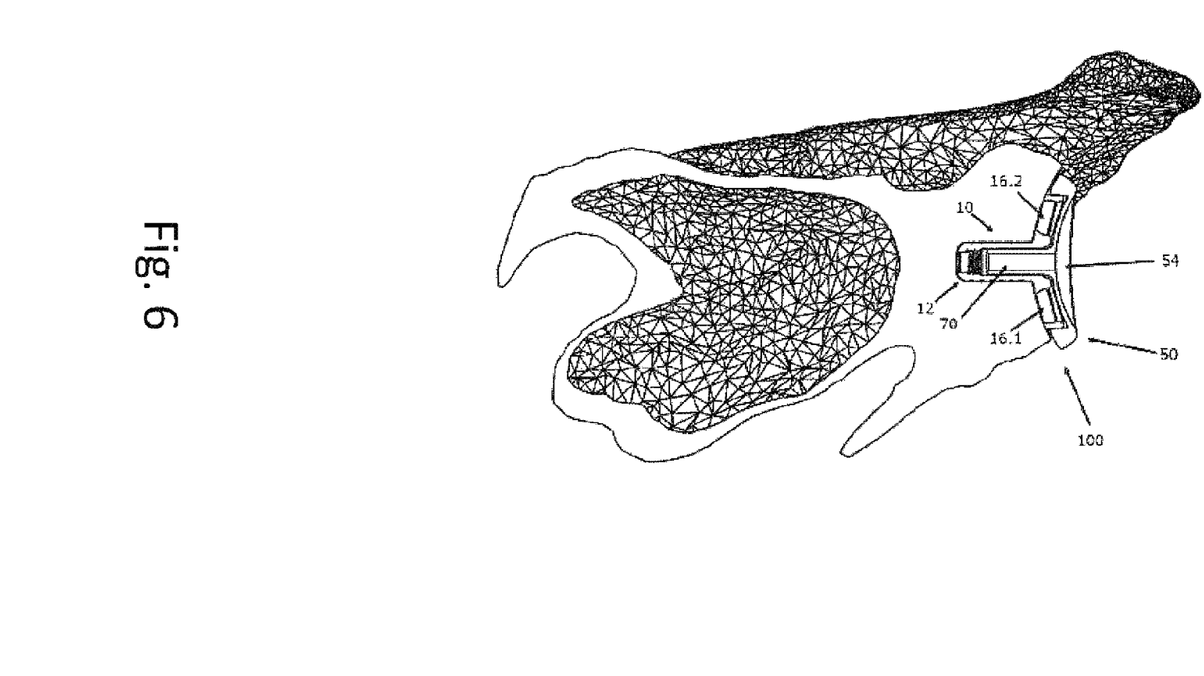
FIG. 6 is a sectional view of a joint prosthesis with removal device put in place in a bone agglomeration.
Figure 7:
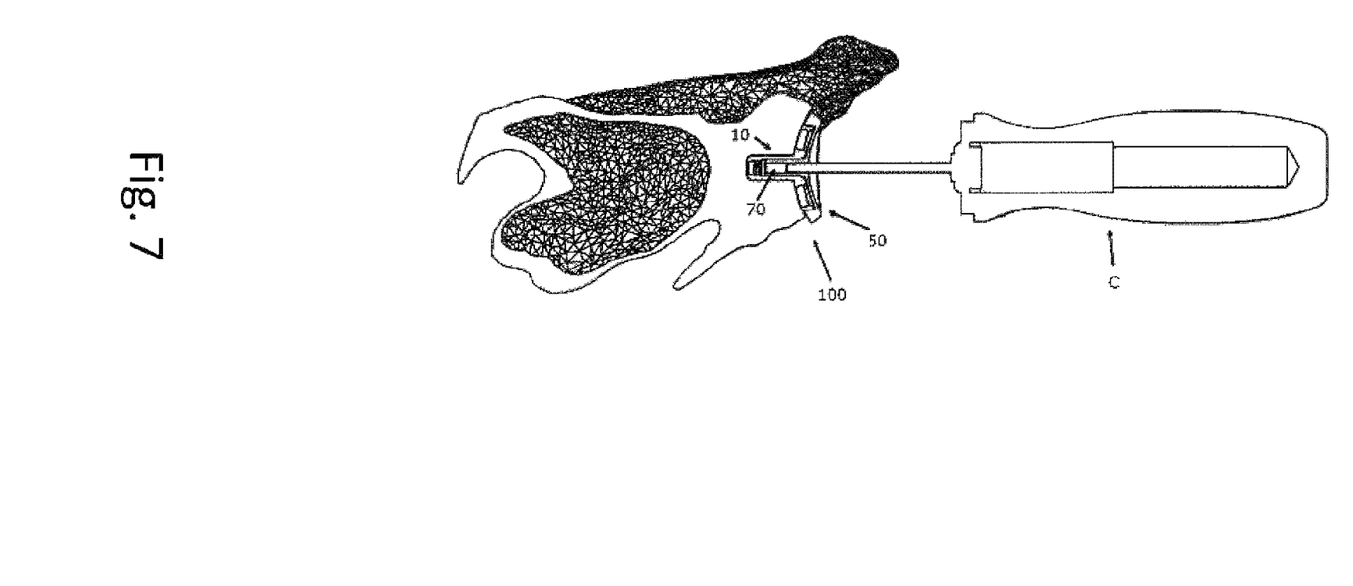
FIG. 7 is a sectional view of a joint prosthesis with removal device during a first step of the disassembly process.
Figure 8:
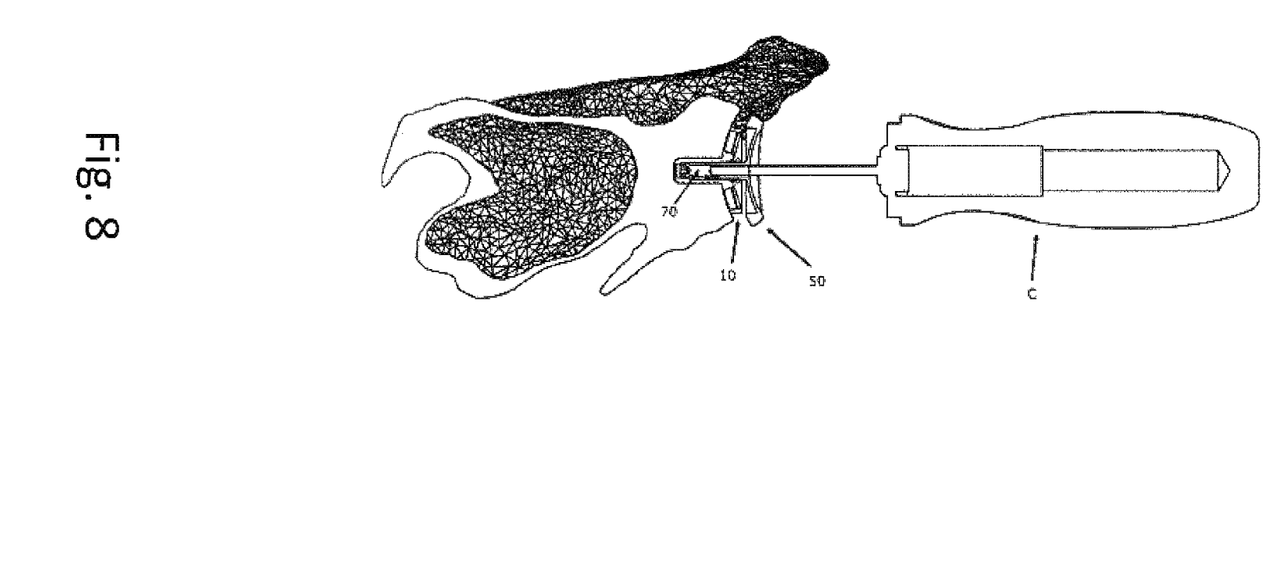
FIG. 8 is a sectional view of a joint prosthesis with removal device during a second step of the disassembly process.
Figure 9:
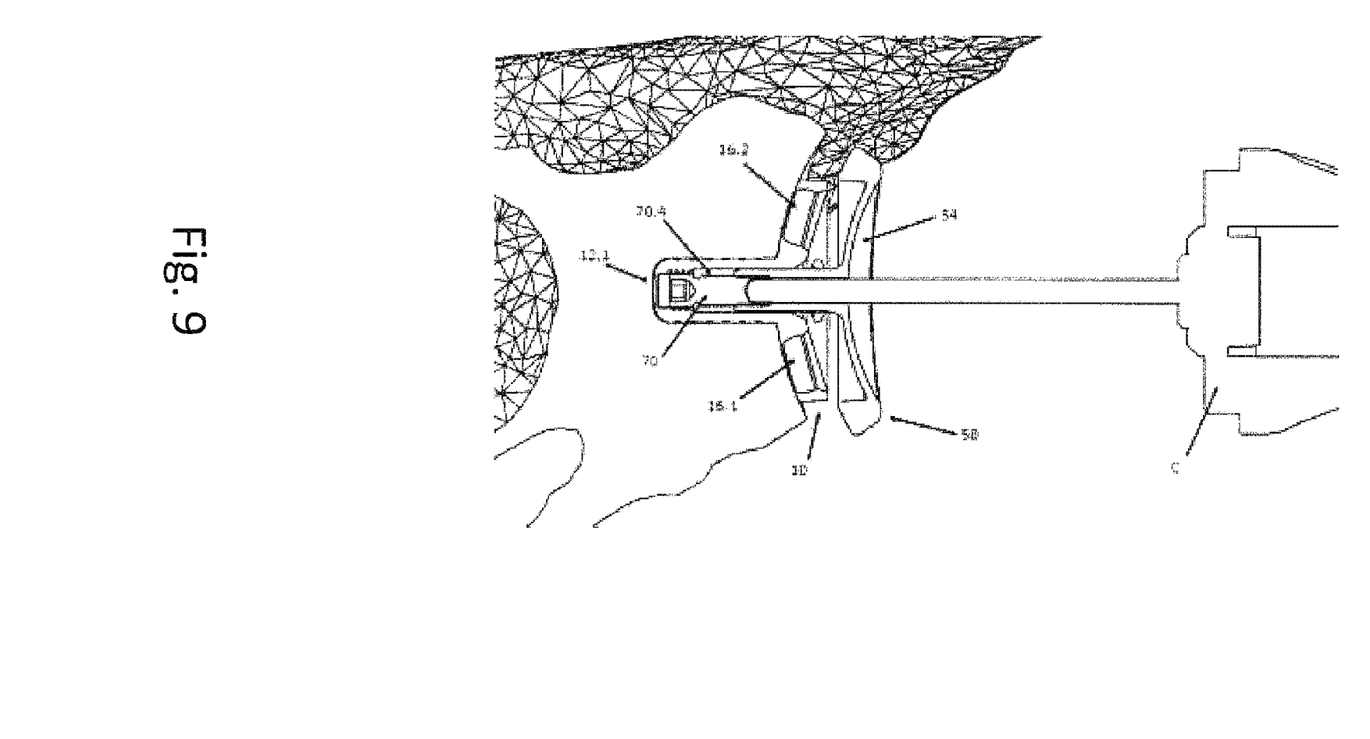
FIG. 9 is a detail view of the particular A of FIG. 8.

In the present description, the terms "medial" and "side" will be also used to denote the parts of the joint prosthesis 100 with removal device that are located in medial or side position with respect to the bone structure on which said device is implanted, as shown in FIGS. 6 to 9. The terms "upper" and "lower" will be used with respect to the assembly direction of the device 100 as shown in FIG. 5.

The joint prosthesis 100 with removal device essentially comprises: a first portion, designated in the following as lower portion 10, a second portion, designated in the following as upper portion 50, and a removal element 70, made, for example, of a metal material, preferably cobalt-chromium alloys, titanium alloys and/or the like.

The upper portion 50 has two parts: a medial stem part 51 and a side part 52, having a substantially elliptical section. Said two parts are mutually integrally connected. The side part 52 is characterised by two faces: a medial face 52.2 and a side face 52.1. Said side face 52.1 in the side part 52 has a substantially elliptical shape, with a tapered lip 53 tapered and a concave, circular-section central area 54. Said central area 54 substantially has a spherical-cap shape and is adapted to receive a leaning humeral head (not shown). The medial face 52.2 in the side part 52 of the upper portion 50 has a housing area 52.3 and, outside of it, one edge 53.1 of lip 53. Said medial face 52.2 is integrally connected, in its central area, to the medial stem part 51.

The medial stem part 51 has a cylindrical shape with an axial cavity 51.4 and two ends: a lower end 51.6, open to ensure access to said axial cavity 51.4, and an upper end 51.5, integrally connected to the medial face 52.2 of the side part 52. Thus, the upper end 51.5 is closed when the prosthesis is in use. Said axial cavity 51.4 of the medial stem part 51 has, therein and for a substantial part of its axial extension, a thread 51.1. At the free end 51.6 of the stem medial part 51 there are two blunted guides 51.2 and 51.3.

It should be noted that the stem medial part 51 is positioned such that the end 51.5 of the through axial cavity 51.4 is centrally aligned with the side part 52, so that the central axis of the axial cavity 51.4 is aligned with the centre of the central area 54.

A removal element 70 is received within said through axial cavity 51.4, for instance by helical coupling with thread 51.1. Said removal element 70 has a substantially cylindrical shape with two free ends: a first free end 70.1, externally projecting through the free end 51.6, and a second free end 70.2, received within the through axial cavity 51.4 of the medial stem part 51. Both free ends 70.1 and 70.2 respectively have a coupling area 70.6 and 70.5 for coupling to a known fixing device, for example a screwdriver or an Allen wrench.

On a substantial part of the outer surface of said removal element 70 there are engagement/coupling means, for example a thread 70.4 adapted for coupling with thread 51.1, provided inside the through axial cavity 51.4. It should be noted that, in a preferred embodiment of the present invention, said thread 70.4 also extends along the outer side surface of the free end 70.2 and does not extend on the outer side surface of the free end 70.1. The lower portion 10 of the surgical prosthesis 100 with removal device also comprises two parts: a side part 11 and a medial part 12. The side part 11 of the lower portion 10 has a shape allowing it to be received within the housing area 52.3 while in the configuration of use. Particularly, said side part 11 has a central area 14. Said central area 14 has a substantially circular, concave section with a central through hole 15 and a plurality of radial holes 16.1, 16.2, 16.3 and 16.4, also passing through the fitting of said lower portion to the patient's bone by special fixing instruments like, for instance, screws known in the art and not illustrated. Integrally connected to said distal part 11 of the lower portion 10 is a medial part 12. The medial part 12 has a cylindrical shape projecting medially from side part 11 and has a closed free end 12.1. The outer surface 12.3 of medial part 12 has a configuration allowing optimal coupling with a special positioning hole formed into the patient's bone by the surgeon during the implant procedure. For example, the outer surface of medial part 12 can be split and/or coated with porous material suitable for osteointegration such as, for example, a known trabecular metal.

The inner part of said medial part 12 has an axial cavity 12.2, blind and extending throughout the length of said medial part 12 and placed in communication with the central through hole 15 of the central area 14 in the side part 11. Said axial cavity 12.2 is adapted to receive therein, in the configuration of use, the medial stem part 51 and the free end 70.1 of the removal element 70 projecting therefrom.

Implant Procedure.

For the implant procedure of the surgical prosthesis 100 with removal device of the present invention, the surgeon provides for an adequate seat into the patient's bone. Said adequate seat can include a substantially cylindrical housing intended to receive the medial part 12 of the lower portion 10, in addition to a spherical cap-shaped housing at least partially adapted to receive the side part 11 of the lower portion 10. In order to secure the lower portion 10, the surgeon proceeds with the insertion of coupling means, e.g. known surgical screws, inside holes 16.1, 16.2, 16.3 16.4, and secures the lower portion 10 to the patient's bone.

In the configuration of use, the upper portion 50 comes already coupled, for example by threaded coupling, with the removal element 70.

The surgeon then proceeds with the coupling of the upper portion 50 with the lower portion 10 by sliding the stem part 51 within the axial cavity 12.2 until the proximal edge 53.1 of lip 53 comes into contact with the edge 14.1 of the central area 14 of the lower portion 10. At this point, by an interference fit, for example with a Morse-cone coupling type, known in the art and not further described, the upper portion 50 and the lower portion 10 are integrally connected to each other.

Operation.

In order to decouple the upper portion 50 from the lower portion 10, the surgeon uses a special instrument or a instrument known in the art such as, for example, a puncher or a drill and/or the like, making a hole central to the concave central area 54 of the upper portion 50. In this way, thanks to the advantageous positioning of the axial cavity 51.4 of the medial stem part 51, which is aligned axially from said concave central area 54, an access pathway to said axial cavity 51.4 and, thus, to the end 70.2 of the removal element 70 therein contained can be created. Then, by a known instrument such as, for example, a screwdriver C (FIG. 7) or an Allen wrench, the surgeon accesses, through the hole just made, the axial cavity 51.4 until engaging the coupling area 70.6 of the removal element 70. At this point, the application of a force to the removal element 70 puts it in relative translation with respect to the medial stem part 51 of the upper portion 50. In this example, the removal element 70 being coupled to the medial stem part 51 by threaded coupling, the surgeon will apply a torque to said removal element 70 to set it in rotation. Said rotation will bring the removal element 70 to translation in the axial direction with respect to the medial stem part 51 in side-medial direction. This translation, however, will be prevented when the removal element 70 comes into contact with the blind medial end of the axial cavity 12.2. The removal element 70 thus comes in abutment against said blind medial end reaching a position known as stop.

Failure of further translating in medial-side direction of the removal element 70 causes transmission of a force, known as release force, having a direction parallel to that of translation just described, but in a medial-side direction, through the threaded coupling between threads 51.1 and 70.4, respectively of the medial stem part 51 and the removal element 70, to the upper portion 50. When this force exceeds the force generated by the interference fit by which the upper portion 50 and lower portion 10 are coupled, the upper portion 50 uncouples from the lower portion 10, allowing the surgeon to extract it without acting in any manner on the patient's bone structure.

As appears clearly from the above description, the present invention provides a surgical prosthesis 100 with removal device, able to achieve the above-listed objects.

First Alternative.

Figure 10:
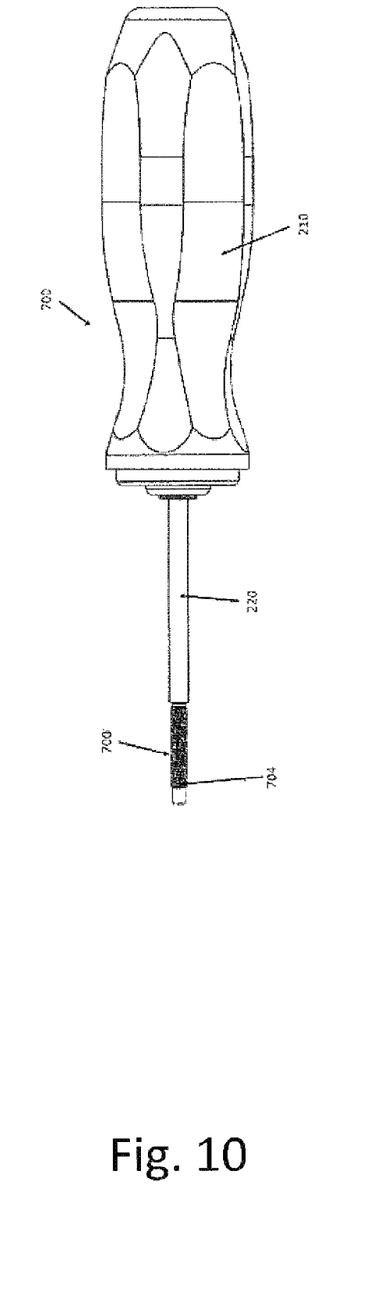
FIG. 10 is a side elevational view of a variant of the preferred embodiment of the present invention.

An alternative embodiment of the present invention is illustrated in FIG. 10. In said FIG. 10 is an instrument 200 incorporating therein the previously described removal element 70. As is readily understandable from mentioned FIG. 10, it comprises: a handle 210, sized and shaped to be comfortably grasped by the surgeon, preferably made of a metal material, having a cylindrical-shaped central portion 220 extending from said handle 210, made of metallic material and having, at its free, integral end, a removal element 700. Said removal element 700 has, for example, engagement/coupling means on its outer surface, for example a thread 704.

Operation

In order to decouple the upper portion 50 from the lower portion 10, the surgeon uses a special instrument or an instrument known in the art such as, for example, a puncher or a drill and/or the like, making a hole central to the concave central area 54 of the upper portion 50. In this way, thanks to the advantageous positioning of the axial cavity 51.4 of the stem medial part 51, which is aligned axially with respect to said concave central area 54, an access pathway to said axial cavity 51.4, thus reaching thread 51.1 present therein, can be created. After reaching said thread 51.1 by acting properly on instrument 200, for example placing it in rotation, thread 704 provided on the outer surface of the removal element 700 integral to said instrument 200 engages thread 51.1. Said rotation will cause translation of the removal element 700 in the axial direction with respect to the medial stem part 51 in side-medial direction. The surgeon will maintain the instrument 200 in rotation until the free end of the engagement element 704 comes into contact with the blind end of the cavity 12.1, thereby achieving a stop position.

Failure of further translating in medial-side direction of the removal element 700 causes transmission of a force, known as release force, having a direction parallel to that of translation just described, but in a medial-side direction, through the threaded coupling between threads 51.1 and 704, respectively of the medial stem part 51 and the removal element 700, to the upper portion 50. When this force exceeds the force generated by the interference fit by which the upper portion 50 and lower portion 10 are coupled, the upper portion 50 uncouples from the lower portion 10, allowing the surgeon to extract it without acting in any manner on the patient's bone structure.

Of course, numerous variations may be made in practice with respect to those described and illustrated by way of non-limiting example, without thereby departing from the scope of the present invention and, therefore, from the domain of the present industrial property right.

The invention claimed is:

1. A joint prosthesis with removal device comprising a first portion suitable to be implanted in a bone structure and suitable to couple with a second portion, wherein the second portion houses within it a removal element suitable to interact with said first portion and/or said second portion and said removal element is translatable with respect to the second portion and is configured to generate a detachment force that actively uncouples the first portion from the second portion of the joint prosthesis, said second portion comprising a medial stem part and a side part, the medial stem part having a cylindrical shape and defining an axial cavity, and the side part having a substantially elliptical section and presenting a medial face and a side face; wherein the medial face faces an opposite axial direction than the side face, said side face has an elliptical shape and said side face defines a concave, circular shaped central area, and the medial stem part extends axially from said medial face of the side part, wherein the removal element is contained, at least partially, inside the axial cavity of the second portion, the removal element comprising a coupling area configured to couple with a fixing device, said coupling area being contained inside the axial cavity of the second portion, wherein the medial stem part has a lower end and an upper end, the lower end being open to ensure access to the axial cavity and the upper end of the medial stem part being closed by and integrally connected to a central area of the medial face of the side part when the prosthesis is in use, the central area of the medial face being axially aligned with the central area of the side face, wherein said first portion has a substantially circular concave central area with a central through hole and a plurality of radial holes.

2. The joint prosthesis with removal device according to claim 1 wherein the detachment force generated by the removal element imposes on the second portion a translation in a direction opposite and parallel to the direction of translation of said removal element relative to the second portion.

3. The joint prosthesis with removal device of claim 1, wherein said axial cavity has means of engagement and/or coupling operationally interposed between the second portion and the removal element.

4. The joint prosthesis with removal device of claim 3, wherein the means of engagement and/or coupling comprise a threading.

5. The joint prosthesis with removal device of claim 3, wherein the removal element has means of engagement and/or coupling suitable to interact with the means of engagement and/or coupling present in the axial cavity of the second portion of the joint prosthesis.

6. The joint prosthesis with removal device of claim 1, wherein the removal element is coupled to the second portion by a helical coupling.

7. The joint prosthesis with removal device of claim 1, wherein the first portion and the second portion are coupled by an interference coupling.

8. The joint prosthesis with removal device of claim 7, wherein the interference coupling between the first portion and the second portion is of the Morse cone type.

9. A method of removing the joint prosthesis of claim 1 by means of the removal element wherein the method comprises:
    opening an access to the axial cavity of the second portion of the joint prosthesis;
    operating the removal element by relatively translating the removal element in relation to the second portion;
    upon reaching of a stop position by the removal element, generating a detachment force, wherein the detachment force causes detachment of the second portion from the first portion of the joint prosthesis.

10. The method of removing the joint prosthesis by means of the removal element according to claim 9 wherein said method further comprises inserting an instrument inside the axial cavity to operate the removal element.

11. A kit comprising the joint prosthesis of claim 1 and an instrument suitable to uncouple the first portion from the second portion of the joint prosthesis.

12. The kit for removing a joint prosthesis according to claim 11 wherein the removal element is coupled to the instrument.

13. The kit for removing a joint prosthesis according to claim 12 wherein the removal element comprises means of engagement/coupling suitable to couple with respective engagement/coupling means of the second portion of the joint prosthesis.

\* \* \* \* \*